United States Patent [19]

Edwards

[11] 4,049,421
[45] Sept. 20, 1977

[54] BACTERICIDAL, FUNGICIDAL AND HERBICIDAL 2-(N,N-DIALKYLAMINO)-3,5-DINITROTHIOPHENES

[75] Inventor: Leroy H. Edwards, Napa, Calif.

[73] Assignee: Chevron Research Company, San Francisco, Calif.

[21] Appl. No.: 699,780

[22] Filed: June 25, 1976

Related U.S. Application Data

[62] Division of Ser. No. 566,568, April 9, 1975, Pat. No. 3,978,083.

[51] Int. Cl.$^2$ .............................................. A01D 9/12
[52] U.S. Cl. ........................................ 71/90; 424/275
[58] Field of Search ............................................ 71/90

[56] References Cited

U.S. PATENT DOCUMENTS

| 3,536,473 | 10/1970 | Popoff et al. | 71/90 |
| 3,819,357 | 6/1974 | Epstein et al. | 71/90 |

OTHER PUBLICATIONS

Renger, Chem. Abst., vol. 77 (1972) 14915d.

*Primary Examiner*—Lewis Gotts
*Assistant Examiner*—Catherine L. Mills
*Attorney, Agent, or Firm*—Dix A. Newell; Raymond Owyang

[57] ABSTRACT

Novel 2-(N,N-dialkylamino)-3,5-dinitrothiophenes have bactericidal, fungicidal and herbicidal activity.

6 Claims, No Drawings

BACTERICIDAL, FUNGICIDAL AND HERBICIDAL 2-(N,N-DIALKYLAMINO)-3,5-DINITROTHIOPHENES

This is a division of application Ser. No. 566,568 filed Apr. 9, 1975, now U.S. Pat. No. 3,978,083.

DESCRIPTION OF THE PRIOR ART

C. D. Hurd and K. L. Kreuz, *J. Am. Chem. Soc.*, 74, 2965 (1952) dicloses 2-amino-3,5-dinitrothiophene. Belgian application No. 756,977, published Oct. 2, 1970, discloses insecticidal 2-(N-arylamino)-3,5-dinitrothiophenes.

DESCRIPTION OF THE INVENTION

It has now been found that 2-(N,N-dialkylamino)-3,5-dinitrothiophenes of the formula (I)

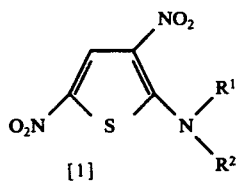

[1]

wherein $R^1$ and $R^2$ individually are methyl or ethyl have high herbicidal activity. The thiophenes of formula (I) are also active fungicides and bactericides.

The thiophenes of formula (I) are prepared by conventional procedures by the reaction of 2-chloro-3,5-dinitrophene and a dialkylamine, as illustrated by the following examples.

EXAMPLES

Example 1

2-(N,N-dialkylamino)-3,5-dinitrothiophene

A solution of 10.4 g (0.05 mol) 2-chloro-3,5-dinitrothiophene, 2.3 g (0.05 mol) dimethylamine, and 5 g (0.05 mol) triethylamine in 150 ml methanol was heated under reflux for ½ hour, cooled and filtered to give 3.5 g of the product, m.p. 146°–148° C. Elemental analysis for $C_6H_7N_3O_4S$ showed: %S, calc. 14.73, found, 15.1.

EXAMPLE 2

2-(N,N-diethylamino)-3,5-dinitrothiophene

A solution of 8.9 g (0.042 mol) 2-chloro-3,5-dinitrothiophene, 6.2 g (0.084 mol) diethylamine and 100 ml methanol was heated under reflux for ½ hour. The reaction mixture was evaporated under reduced pressure, washed with water and extracted with ether. The ether extracts were dried and evaporated to give an oil. The oil was chromatographed on silica gel (30% ether-hexane eluant) to give 7.0 g of product as an amber oil. Elemental analysis for $C_8H_{11}N_3O_4S$ showed: %S, calc. 13.05, found 13.05.

UTILITY

The thiophene compounds of the present invention are, in general, herbicidal in both pre- and post-emergent applications. For pre-emergent control of undesirable vegetation, the compounds will be applied in herbicidal quantities to the environment or growth medium of the vegetation, e.g., soil infested with seeds and/or seedlings of such vegetation. Such application will inhibit the growth of or kill the seeds, germinating seeds and seedlings. For post-emergent applications, the compounds of the present invention will be applied directly to the foliage and other plant parts. Generally they are effective against weed grasses as well as broadleaved weeds. The compounds are particularly effective as pre-emergent herbicides.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carries include water and organic solvents, e.g., hydrocarbons such as benzene, toluene, kerosene, diesel oil, fuel oil, and petroleum naphtha. Suitable solid carriers are natural clays such as kaolinite, atalpulgite, and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as a solid carrier.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application — i.e., sheltered areas such as greenhouses, as compared to exposed areas such as fields — as well as the desired type of control. Generally, for both pre- and post-emergent control, the herbicidal compounds of the invention are applied at rates of 0.1 to 10 lbs/acre, and the preferred rate is in the range of 2 to 5 lbs/acre.

Pre-emergent herbicidal tests on representative compounds of this invention were made using the following method:

An acetone solution of the test thiophene was prepared by mixing 750 mg thiophene, 220 mg of a nonionic surfactant and 25 ml of acetone. This solution was added to approximately 125 ml of water containing 156 mg of surfactant.

Seeds of the test vegetation were planted in pots of soil and the solution was sprayed uniformly onto the soil surface at a dose of 1.2γ per cm² (0.1 lb/acre) to 33γ per cm² (3 lbs/acre). The pots were watered and placed in a greenhouse. The pots were watered intermittently and were observed for seedling emergence, health of emerging seedlings, etc., for a 3-week period. At the end of this period the herbicidal effectiveness of the solutions was rated based on the physiological observations. A 0-to-100 scale was used, 0 representing no phytotoxicity, 100 representing complete kill. The results are tabulated in Table 1. For comparison, several structurally related thiophene compounds were also tested.

TABLE I

Herbicidal Effectiveness of 2,5-Dinitro-thiophenes of the formula

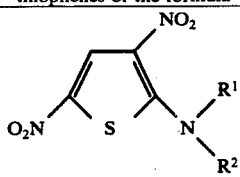

| No. | R¹ | R² | Dose, γ/cm² | O | W | C | M | P | L |
|---|---|---|---|---|---|---|---|---|---|
| 1 | CH$_3$ | CH$_3$ | 33 | 70 | 100 | 100 | 100 | 100 | 100 |
|   |    |    | 11 | 23 | 100 | 100 | 99 | 100 | 98 |
|   |    |    | 3.7 | 7 | 53 | 90 | 37 | 100 | 97 |
|   |    |    | 1.2 | 0 | 12 | 50 | 0 | 92 | 99 |
| 2 | C$_2$H$_5$ | C$_2$H$_5$ | 33 | 0 | 70 | 90 | 100 | 100 | 100 |
|   |    |    | 11 | 3 | 20 | 53 | 73 | 93 | 93 |
|   |    |    | 3.7 | 0 | 17 | 20 | 17 | 77 | 90 |
|   |    |    | 1.2 | 0 | 7 | 13 | 13 | 70 | 72 |
| 3 | nC$_3$H$_7$ | nC$_3$H$_7$ | 33 | 0 | 0 | — | 0 | 0 | — |
| 4 | nC$_4$H$_9$ | nC$_4$H$_9$ | 33 | 0 | 0 | 0 | 0 | 0 | 0 |
| 5 | H | C$_2$H$_5$ | 33 | 0 | 0 | — | 0 | 0 | 0 |
| 6 | H | iC$_3$H$_7$ | 33 | 0 | 0 | 0 | 0 | 0 | 0 |

O = Wild Oats (*Avenua fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

The thiophene compounds of the invention are also useful for controlling pathogens such as bacteria and fungi. For example, 2-(N,N-dimethylamino)-3,5-dinitrothiophene was effective for the control of fungi such as *Phytophthora infestans*, *Alternaria solani* and *Erysiphe polygoni*, and for the control of bacteria such as *Erwinia amylovora*, *Pseudomonas syringe* and *Xanthomonas vesicatoria*.

When used as fungicides or bactericides, the thiophenes of this invention will be formulated and applied in fungicidally or bactericidally effective amounts by conventional art methods to fungi, bacteria, or hosts which are subject to fungal or bacterial attack. They may be combined with inert liquids and solid carriers as powders, solutions or dispersions for such use.

What is claimed is:

1. A method for controlling the growth of undesirable vegetation which comprises applying to the vegetation or the growth medium thereof an herbicidally effective amount of the compound of the formula wherein R¹ and R² individaully are methyl or ethyl.

2. The method of claim 1 wherein the compound is 2-(N,N-dimethylamino)-3,5-dinitrothiophene.

3. The method of claim 1 wherein the compound is 2-(N,N-diethylamino)-3,5-dinitrothiophene.

4. An herbicidal composition comprising a biologically inert carrier and an herbicidally effective amount of the compound of Claim 1.

5. The composition of claim 4 wherein the compound is 2-(N,N-dimethylamino)-3,5-dinitrothiophene.

6. The composition of claim 4 wherein the compound is 2-(N,N-diethylamino)-3,5-dinitrothiophene.

* * * * *